(12) United States Patent
Biernacki et al.

(10) Patent No.: US 7,399,482 B1
(45) Date of Patent: Jul. 15, 2008

(54) THIN FILM MEDICATION DEVICE AND KIT

(76) Inventors: Christine Horner Biernacki, 245 Valhalla DR., Deland, FL (US) 32724; Carolyn Horner Palank, 155-A Awaiku St., Lahaina, HI (US) 96761

( * ) Notice: Subject to any disclaimer, the term of this patent is extended or adjusted under 35 U.S.C. 154(b) by 817 days.

(21) Appl. No.: 10/841,356

(22) Filed: May 7, 2004

(51) Int. Cl.
*A61K 47/00* (2006.01)
(52) U.S. Cl. ..................................... 424/439
(58) Field of Classification Search ................ 424/422, 424/434, 439–441, 443
See application file for complete search history.

(56) References Cited

U.S. PATENT DOCUMENTS

| | | | |
|---|---|---|---|
| 1,642,653 A | 9/1927 | Goldstein | |
| 4,925,670 A | 5/1990 | Schmidt | |
| 5,122,383 A * | 6/1992 | Heiber et al. | 424/449 |
| 5,354,551 A | 10/1994 | Schmidt | |
| 5,529,782 A | 6/1996 | Staab | |
| 5,700,478 A * | 12/1997 | Biegajski et al. | 424/434 |
| 6,177,096 B1 | 1/2001 | Zerbe et al. | |
| 6,419,903 B1 | 7/2002 | Xu et al. | |
| 6,803,420 B2 * | 10/2004 | Cleary et al. | 525/205 |
| 2002/0162874 A1* | 11/2002 | Spolidoro et al. | 226/20 |

* cited by examiner

*Primary Examiner*—Sharon E. Kennedy

(57) ABSTRACT

A thin layer medication device and kit for various therapeutic uses are disclosed. The device includes at least one support sheet and at least one application strip attached to the support sheet, wherein the strip includes a polymer base and a therapeutic agent admixed with the polymer base. The kit includes a plurality of support sheets, a plurality of application strips attached to each support sheet; and a case containing the plurality of support sheets.

18 Claims, 8 Drawing Sheets

THIN FILM MEDICATION DEVICE AND KIT

FIELD OF THE INVENTION

The present invention relates therapeutic medication delivery devices. More particularly, to a thin film medication device and kit for use in providing a convenient and effective means for delivering a wide variety of medications into a patient via a moistened membrane tissue structure such as the oral mucosa by applying the dose strips onto the surface of the tongue or inside surfaces of the cheek or gums for maximum and efficient absorption.

BACKGROUND OF THE INVENTION

A wide variety of medication devices is currently available on the commercial market and an even larger number of these types of devices are known in the art of medication devices, for example, pills, elixirs, solutes, cocktails, powders, and hypodermic needle/syringes. Successful application of the various therapeutic components requires adsorption into the patient. Unfortunately, a number of difficulties hinder the successful application of these therapeutic compounds, such as the difficulty in swallowing pills containing these therapeutic compounds.

While all of the above-described devices fulfill their respective, particular objectives and requirements, the aforementioned patents do not describe a thin film medication device having at least one support sheet and at least one application strip attached to the support sheet, wherein the strip includes a polymer base and a therapeutic agent admixed with the polymer base. This combination of elements would specifically match the user's particular individual needs of making it possible to conveniently deliver a wide variety of medications into a patient via a moistened membrane tissue structure such as the oral mucosa by applying the dose strips onto the surface of the tongue or inside surfaces of the cheek or gums for maximum and efficient absorption. The above-described patents make no provision for a thin film medication device having at least one support sheet and at least one application strip attached to the support sheet, wherein the strip includes a polymer base and a therapeutic agent admixed with the polymer base.

Therefore, a need exists for a new and improved thin film medication device having at least one support sheet and at least one application strip attached to the support sheet, wherein the strip includes a polymer base and a therapeutic agent admixed with the polymer base. In this respect, the thin film medication device according to the present invention substantially departs from the conventional concepts and designs of the prior art, and in doing so provides an apparatus primarily developed for the purpose of providing a convenient means for delivering a wide variety of medications into a patient via a moistened membrane tissue structure such as the oral mucosa by applying the dose strips onto the surface of the tongue or inside surfaces of the cheek or gums for maximum and efficient absorption.

SUMMARY OF THE INVENTION

The present device, kit and method of using, according to the principles of the present invention, overcomes the shortcomings of the prior art by providing a novel and nonobvious thin film medication device, kit and method of using the same. The device includes at least one support sheet and at least one application strip attached to the support sheet, wherein the strip includes a polymer base and a therapeutic agent admixed with the polymer base. The kit includes a plurality of support sheets, a plurality of application strips attached to each support sheet; and a case containing the plurality of support sheets.

In view of the foregoing disadvantages inherent in the known type medication devices now present in the prior art, the present invention provides an improved thin film medication device, which will be described subsequently in great detail, is to provide a new and improved thin film medication device which is not anticipated, rendered obvious, suggested, or even implied by the prior art, either alone or in any combination thereof.

To attain this, the present invention essentially comprises at least one support sheet and at least one application strip attached to the support sheet, wherein the strip includes a polymer base and a therapeutic agent admixed with the polymer base.

There has thus been outlined, rather broadly, the more important features of the invention in order that the detailed description thereof that follows may be better understood, and in order that the present contribution of the art may be better appreciated.

The invention may also include a case. There are of course, additional features of the invention that will be described hereinafter and which will form the subject matter of the claims attached.

Numerous objects, features and advantages of the present invention will be readily apparent to those of ordinary skill in the art upon reading of the following detailed description of presently preferred, but nonetheless illustrative, embodiments of the present invention when taken in conjunction with the accompany drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved thin film medication device that has all the advantages of the prior art thin film medication device and none of the disadvantages.

It is another object of the present invention to provide a new and improved thin film medication device that may be easily and efficiently manufactured and marketed.

An even further object of the present invention is to provide a new and improved thin film medication device that has a low cost of manufacture with regard to both materials and labor, and which accordingly is then susceptible of low prices of sale to the consuming public, thereby making such multipurpose storage unit and system economically available to the buying public.

Still another object of the present invention is to provide a new thin film medication device that provides in the apparatuses and methods of the prior art some of the advantages thereof, while simultaneously overcoming some of the disadvantages normally associated therewith.

Even still another object of the present invention is to provide a thin film medication device having at least one support sheet and at least one application strip attached to the support sheet, wherein the strip includes a polymer base and a therapeutic agent admixed with the polymer base. This combination of elements makes it possible to conveniently deliver a wide variety of medications into a patient via a moistened membrane tissue structure such as the oral mucosa by applying the dose strips onto the surface of the tongue or inside surfaces of the cheek or gums for maximum and efficient absorption.

Lastly, it is an object of the present invention to provide a kit comprising a plurality of support sheets, a plurality of application strips attached to each support sheet; and a case containing the plurality of support sheets.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and description matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DETAILED DESCRIPTION OF THE PREFERRED EMBODIMENT

Figure 1:
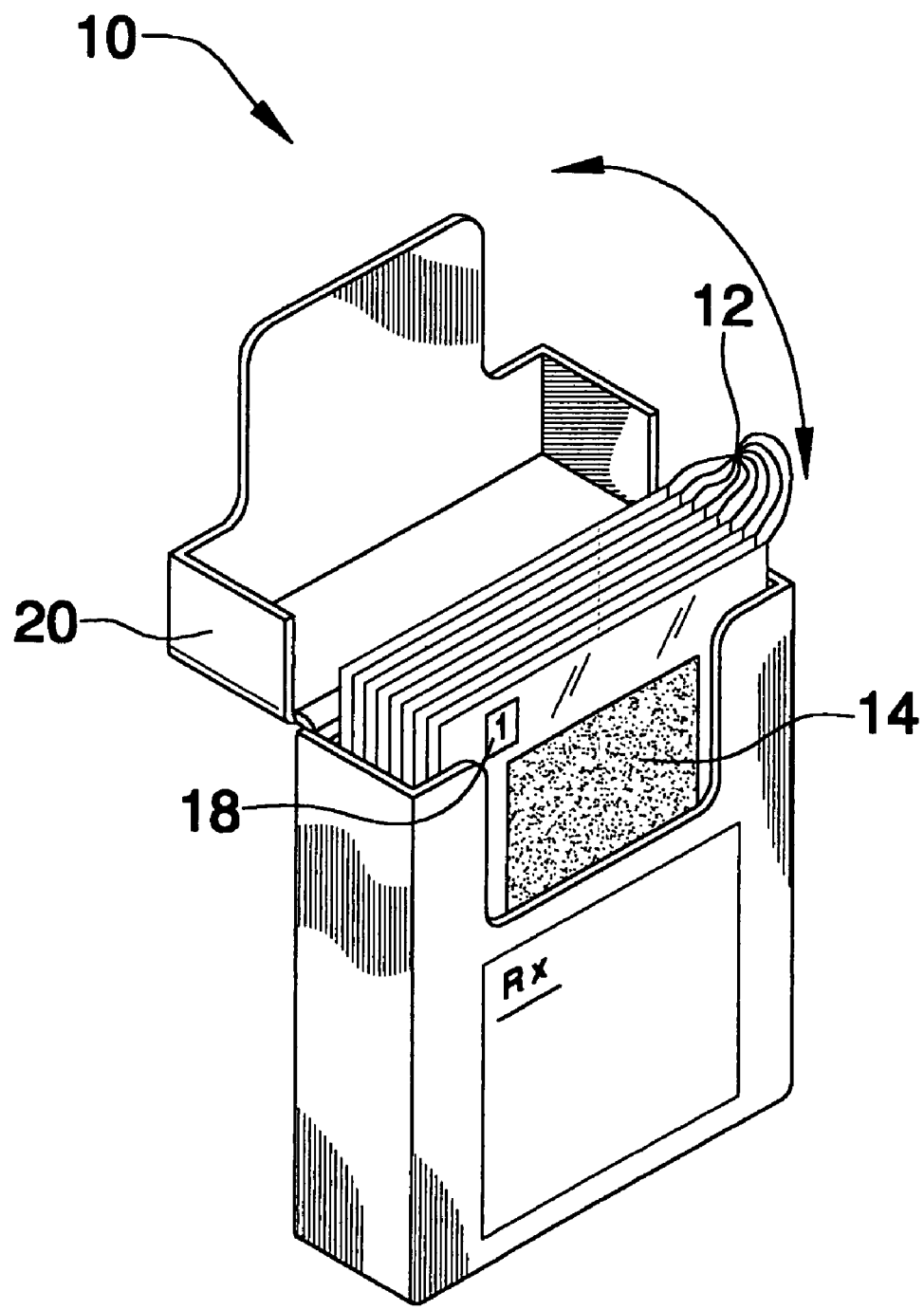
FIG. 1 is a perspective view of an preferred embodiment of the thin film medication device constructed in accordance with the principles of the present invention.

Referring now to the drawings, and in particular FIGS. 1 to 8 thereof, one preferred embodiment of the present invention is shown and generally designated by the reference numeral 10. One preferred embodiment of thin film medication device 10 for therapeutic use comprises: at least one support sheet 12; and at least one application strip 14 attached to the support sheet 12, the strip 14 comprising: a polymer base; and a therapeutic agent admixed with the polymer base.

Another preferred embodiment of thin film medication device 10 for therapeutic use consists essentially of: at least one support sheet 12; and at least one application strip 14 attached to the support sheet 12, the strip 14 comprising: a polymer base; and a therapeutic agent admixed with the polymer base.

An optional coloring agent may be added to the device 10 wherein the coloring agent is admixed with the polymer base of the strip 14 wherein the coloring agent is selected from the group consisting of FD&C Blue No. 1, FD&C Blue No. 2, FD&C Green No. 1, FD&C Green No. 2, FD&C Green No. 3, FD&C Orange No. 1, FD&C Red No. 1, FD&C Red No. 2, FD&C Red No. 3, FD&C Red No. 4, FD&C Red No. 32, FD&C Red No. 40, FD&C Yellow No. 1, FD&C Yellow No. 3, FD&C Yellow No. 4, FD&C Yellow No. 5, FD&C Yellow No. 6, and mixtures thereof.

An optional sweetening agent may be added to the device 10 wherein the sweetening agent is admixed with the polymer base of the strip 14, wherein the sweetening agent is selected from the group consisting of saccharin, aspartame, acesulfame K, sucrose, fructose, glucose, maltose, maltooligosaccharides, invert sugars, isomaltooligosaccharides, saccharified starch, isomerized sugars, dextrose, and mixtures thereof.

An optional conjugating agent may be added to the device 10 wherein the conjugating agent is admixed with the polymer base of the strip 14, wherein the conjugating agent is selected from the group consisting of ascorbic acid, sodium ascorbate, potassium ascorbate, calcium ascorbate, and mixtures thereof.

An optional osmotic disruptor may be added to the device 10 wherein the osmotic disruptor is admixed with the polymer base of the strip 14, wherein the osmotic disrupter is mannitol.

An optional cover 16 may be added to the device 10 wherein the cover 16 is reversibly attached to the support sheet 12 and attached to the strip 14, wherein the cover 16 is removable from the support sheet 12 and from the strip 14. One preferred configuration of the optional cover 16 is that it is made of transparent cellophane which hermetically seals the strip 14.

An optional label 18 may be added to the device 10 wherein label 18 is affixed onto the support sheet 12.

An optional plurality of application strips 14 may be added to the device 10 in which the plurality of application strips 14 are attached to the support sheet 12.

An optional case 20 may be added to the device 10 wherein the case 20 contains the support sheet 12.

An optional plurality of support sheets 12 may be added to the device 10.

The polymer base of the strip 14 of the device 10 may be selected from any known commercially available polymeric base. One preferred configuration of the polymeric base is that it is selected from the group consisting of a starch-based polymer, a lipid-based polymer, a glycerin-based polymer, a protein-based polymer (including gelatin-based polymers) and mixtures thereof. Another preferred configuration of the polymeric base is that it is selected from the group consisting of pullulan, hydroxypropylmethyl cellulose, hydroxyethyl cellulose, hydroxypropyl cellulose, polyvinyl pyrrolidone, carboxymethyl cellulose polyvinyl alcohol sodium alginate, polyethylene glycol, xanthane gum, tragacantha guar gum, acacia gum, arabic gum, polyacrylic acid, methylmethacrylate copolymer carboxyvinyl polymer and copolymers and mixtures thereof. A most preferred configuration of the polymer base of the strip 14 is that it comprises a hexatic phase micro thin material with an amorphous molecular orientation.

The therapeutic agent may be selected from any known commercially available therapeutic agent material. One preferred configuration of the therapeutic agent is that it selected from the group consisting of an analgesic, a non-steroidal anti-inflammatory agent, a steroid, a hormone, an antihistamine, a tranquilizer, an antidepressant, a hypnotic, a sedative, an antiepileptic, an awakening agent, a psychoneurotropic agent, a neuromuscular blocking agent, an antispasmodic agent, an antihistaminic, an antiallergic, a cardiotonic, an antiarhythmic, a diuretic, a hypotensive, a vasopressor, an antitussive expectorant, a thyroid hormone, a sexual hormone, an antidiabetic, an antitumor agent, an antibiotic, a chemotherapuetic, a narcotic, a vaccine, a probiotic microorganism, and mixtures thereof. The probiotic microorganism configuration of the therapeutic agent may be selected from the group consisting of *Lactobacillus acidophilus, Lactobacillus casei, Lactobacillus paracasei, Lactobacillus pediocci, Bifidobacterium bifidus, Bifidobacterium longum, Enterococcus faecium*, and *Saccharomyces boulardii*.

One preferred compositional weight ratio of the strip is that the polymer base comprising about 40 to about 80 wt % of the strip 14; and the therapeutic agent comprising about 20 to about 40 wt % of the strip 14.

The geometric shape of each strip 14 of the device 10 may have any known geometric shape. One preferred configuration of the geometric shape of each strip 14 of the device is that it is selected from the group consisting of a stylized heart, a stylized flower, and a stylized star.

One preferred embodiment of a kit for a thin film medication device 10 for therapeutic use comprises: a plurality of support sheets 12; and a plurality of application strips 14 attached to each support sheet 12, each strip 14 comprising: a polymer base comprising about 40 to about 80 wt % of the strip 14; and a therapeutic agent admixed with the polymer base of the strip 14 wherein the therapeutic agent comprising about 20 to about 40 wt % of the strip 14, wherein the therapeutic agent is a probiotic microorganism selected from the group consisting of *Lactobacillus acidophilus, Lactobacillus casei, Lactobacillus paracasei, Lactobacillus pediocci, Bifidobacterium bifidus, Bifidobacterium longum, Enterococcus faecium*, and *Saccharomyces boulardii*; and a case 20 containing the plurality of support sheets 12.

Referring now to FIG. 1 which depicts a perspective view of an preferred embodiment of the thin film medication device 10 showing a plurality of support sheets 12; an application strip 14 attached to one of the support sheets 12, a label 18 affixed to one of the sheets 12, and a case holding the plurality of support sheets 12.

Figure 2:
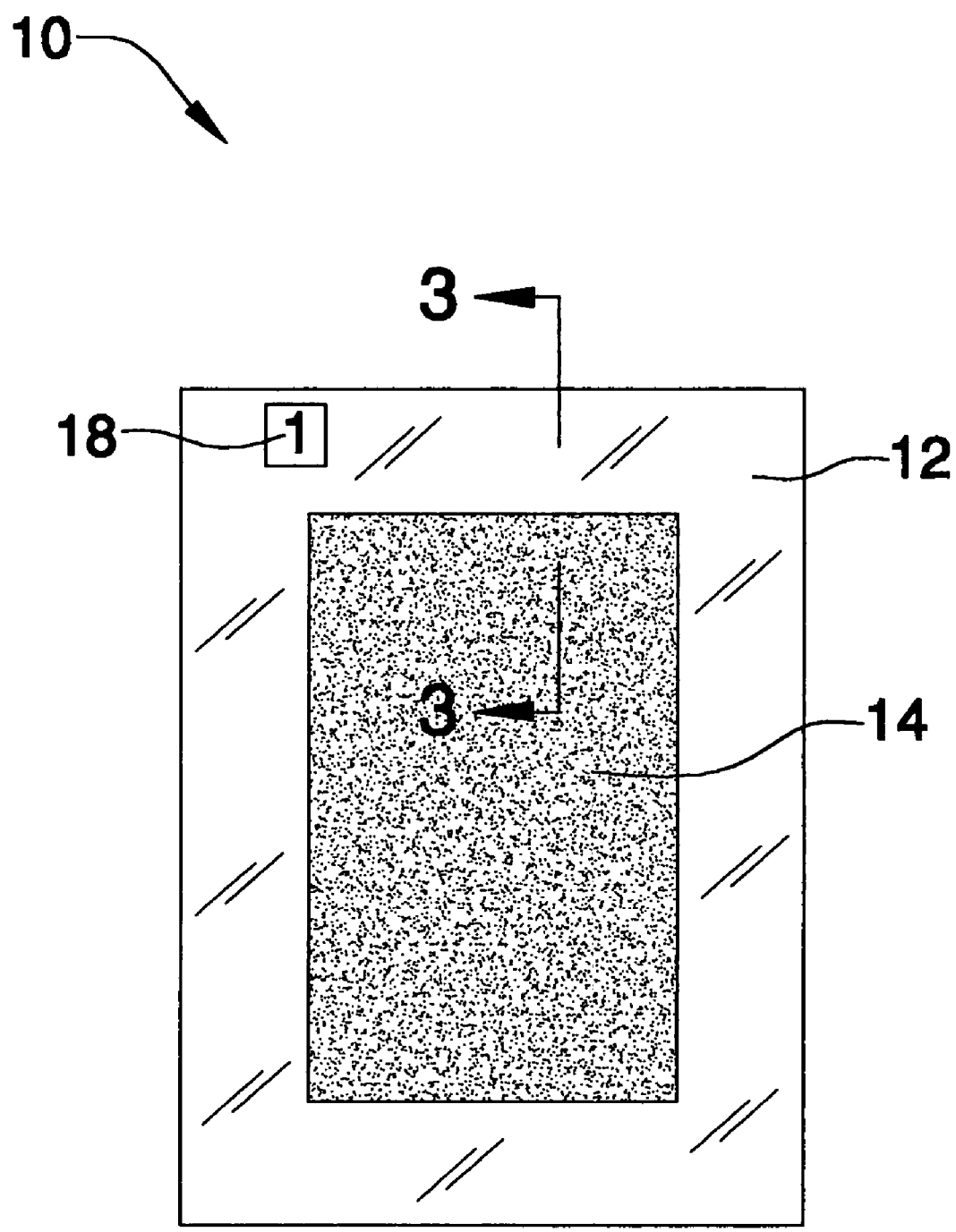
FIG. 2 is a frontview of a preferred embodiment of the thin film medication device of the present invention.

Referring now to FIG. 2 which depicts a front view of a preferred embodiment of the thin film medication device 10 showing one support sheet 12 with one application strip 14 attached to the support sheet 12 and a label 18 affixed to one of the sheets 12.

Figure 3:
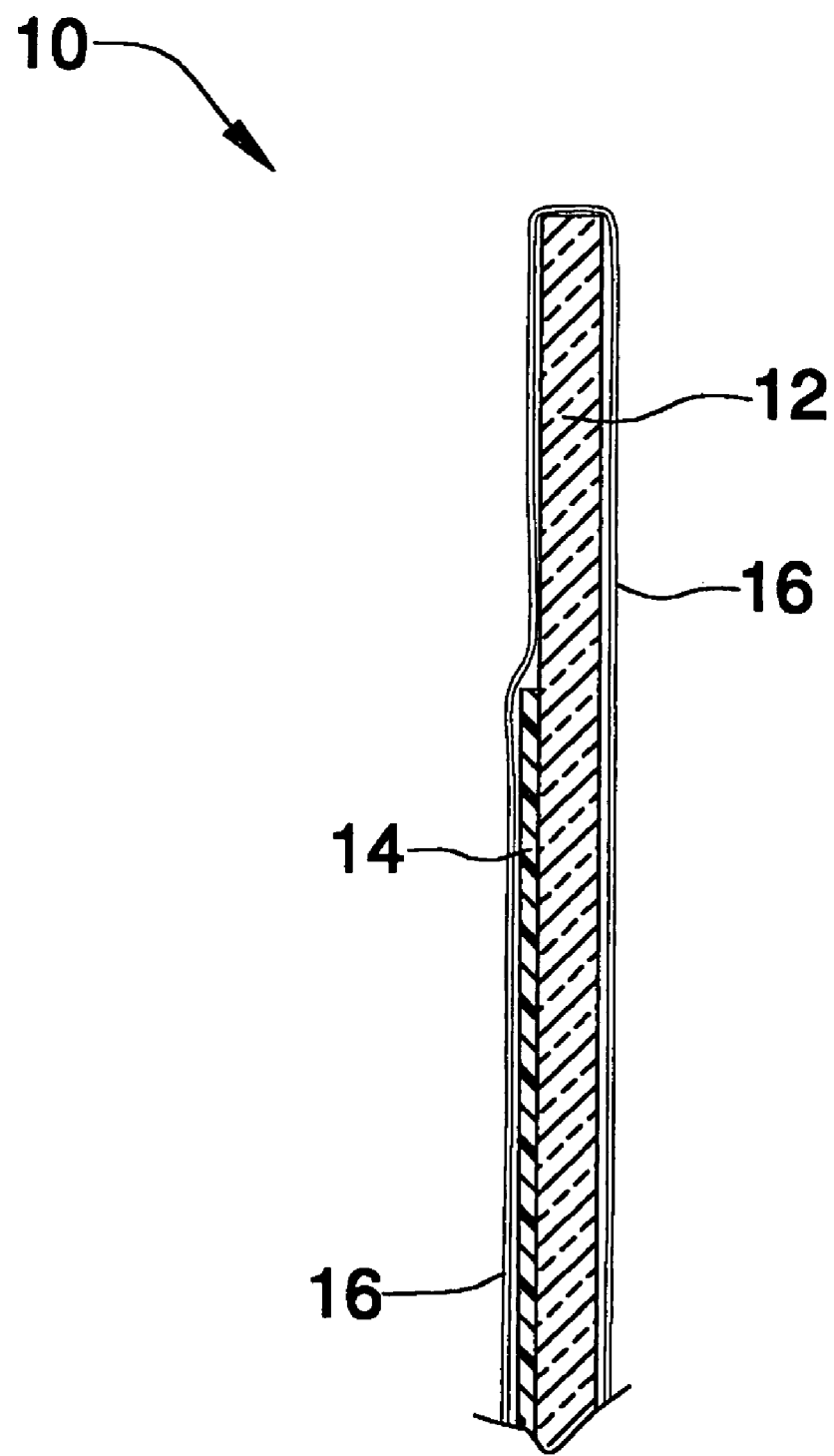
FIG. 3 is a cross sectional side view of a preferred embodiment of the thin film medication device of the present invention.

Referring now to FIG. 3 which depicts a cross sectional side view of a preferred embodiment of the thin film medication device 10 showing a support sheet 12; an application strip 14 attached to the support sheet 12, and a cover 16 which is reversibly attached to the support sheet 12 and attached to the strip 14, wherein the cover 16 is removable from the support sheet 12 and from the strip 14.

Figure 4:
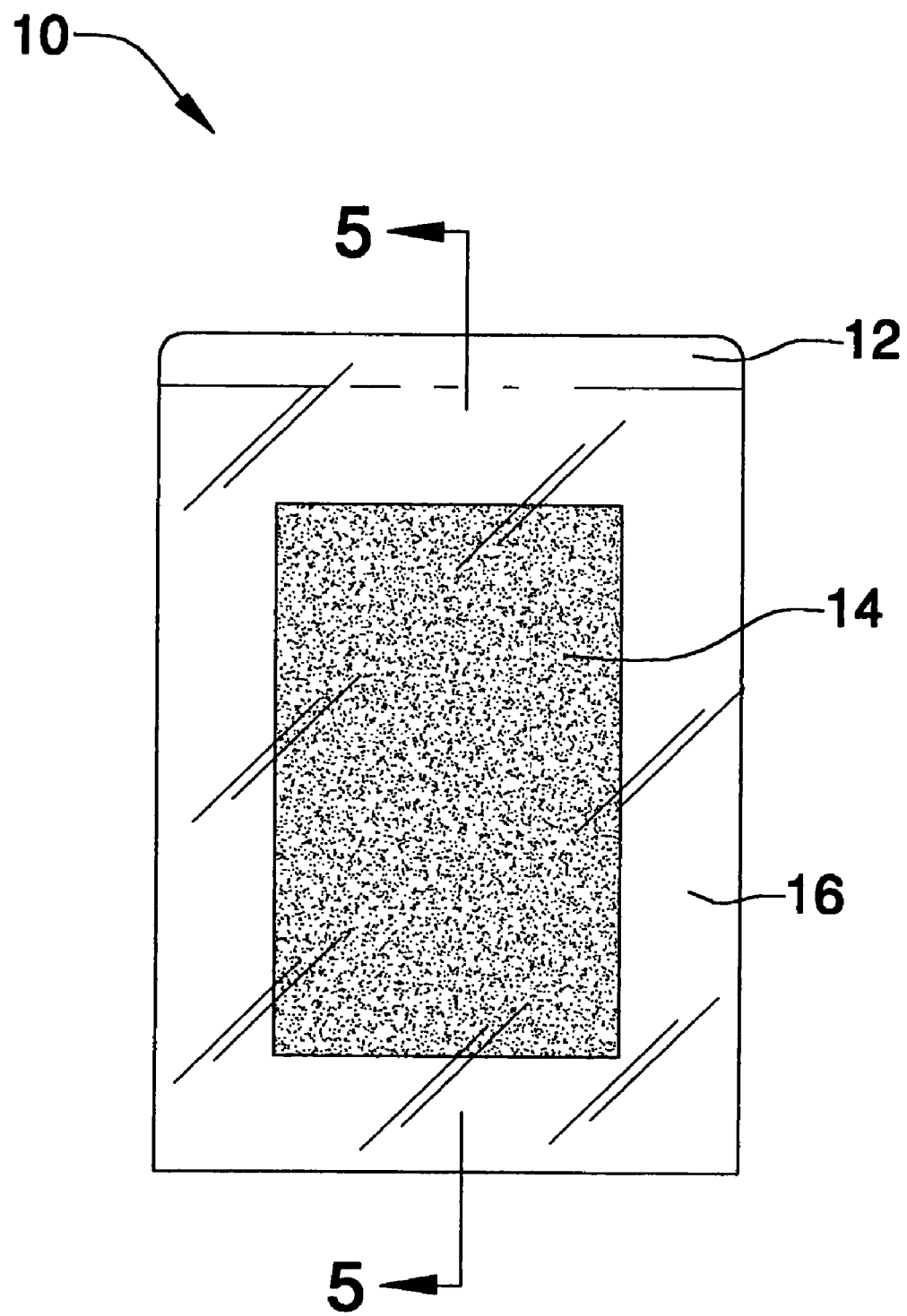
FIG. 4 is a front view of a preferred embodiment of the thin film medication device of the present invention.

Referring now to FIG. 4 which depicts a front view of a preferred embodiment of the thin film medication device 10 showing a support sheet 12; an application strip 14 attached to the support sheet 12, and a semi-transparent cover 16 which reversibly attached to the support sheet 12 and attached to the strip 14, wherein the cover 16 is removable from the support sheet 12 and from the strip 14.

Figure 5:
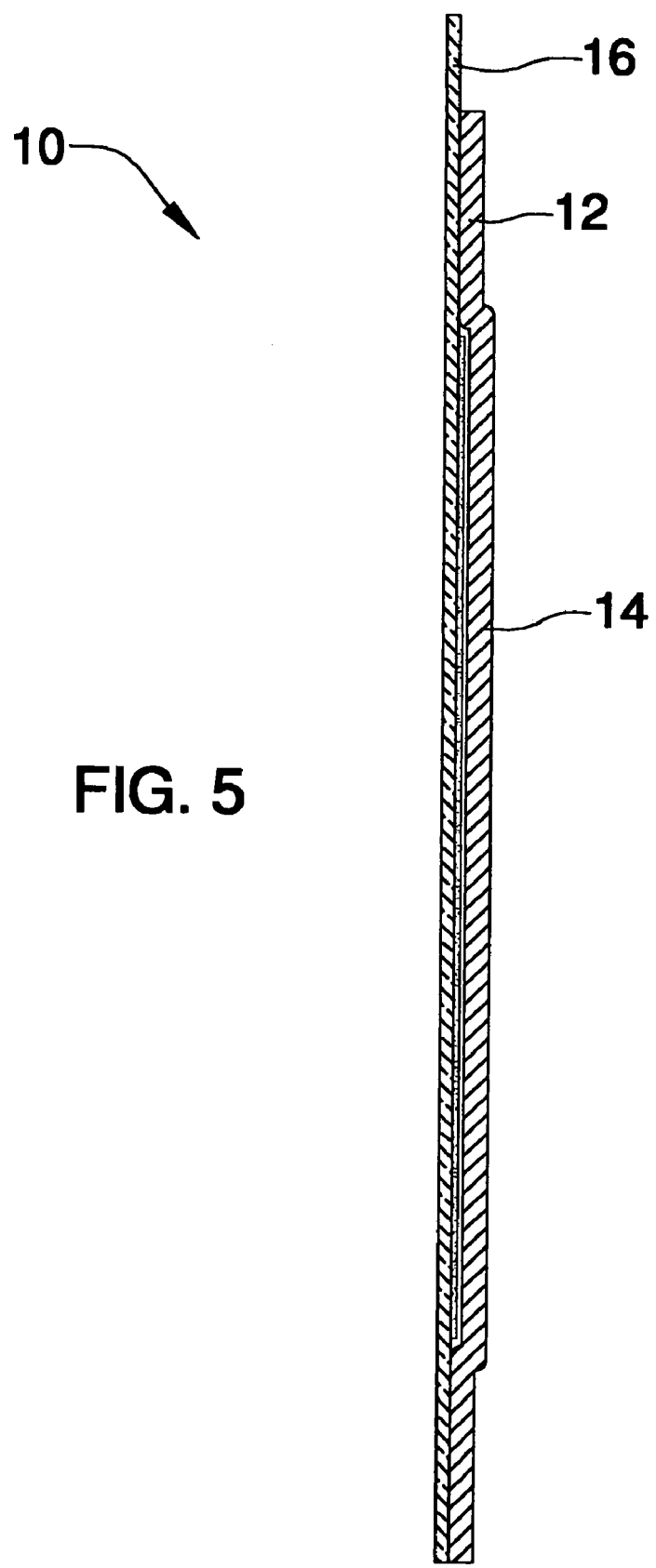
FIG. 5 is a cross sectional side view of a preferred embodiment of the thin film medication device of the present invention.

Referring now to FIG. 5 which depicts a cross sectional side view of a preferred embodiment of the thin film medication device 10 showing a support sheet 12; an application strip 14 attached to the support sheet 12, and a semi-transparent cover 16 which is reversibly attached to the support sheet 12 and attached to the strip 14, wherein the cover 16 is removable from the support sheet 12 and from the strip 14.

Figure 6:
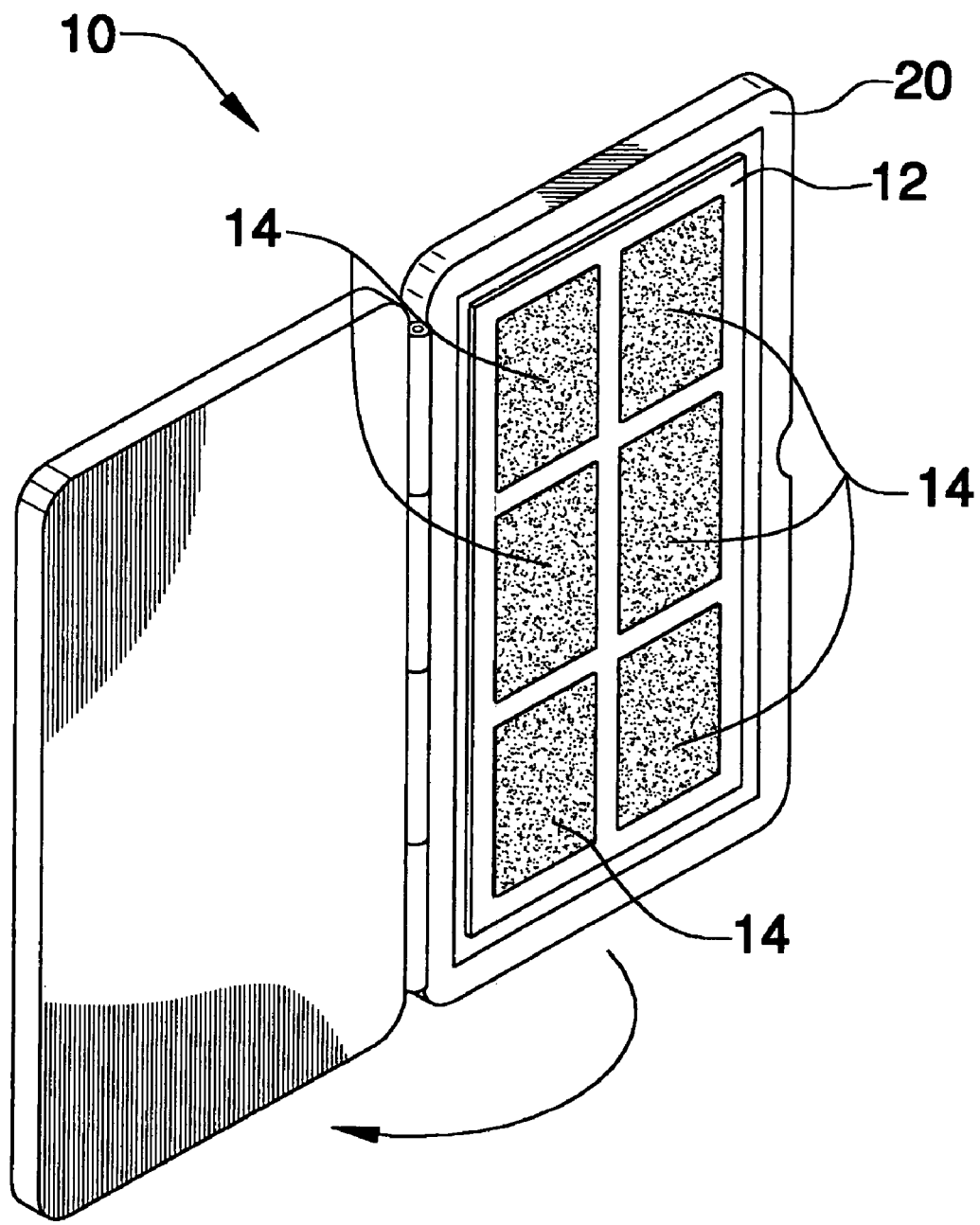
FIG. 6 is a perspective view of a preferred embodiment of the thin film medication device of the present invention.

Referring now to FIG. 6 which depicts a perspective view of a preferred embodiment of the thin film medication device 10 showing a support sheet 12; a plurality of application strips 14 attached to the support sheet 12, and a case 20 containing the support sheet 12.

Figure 7:
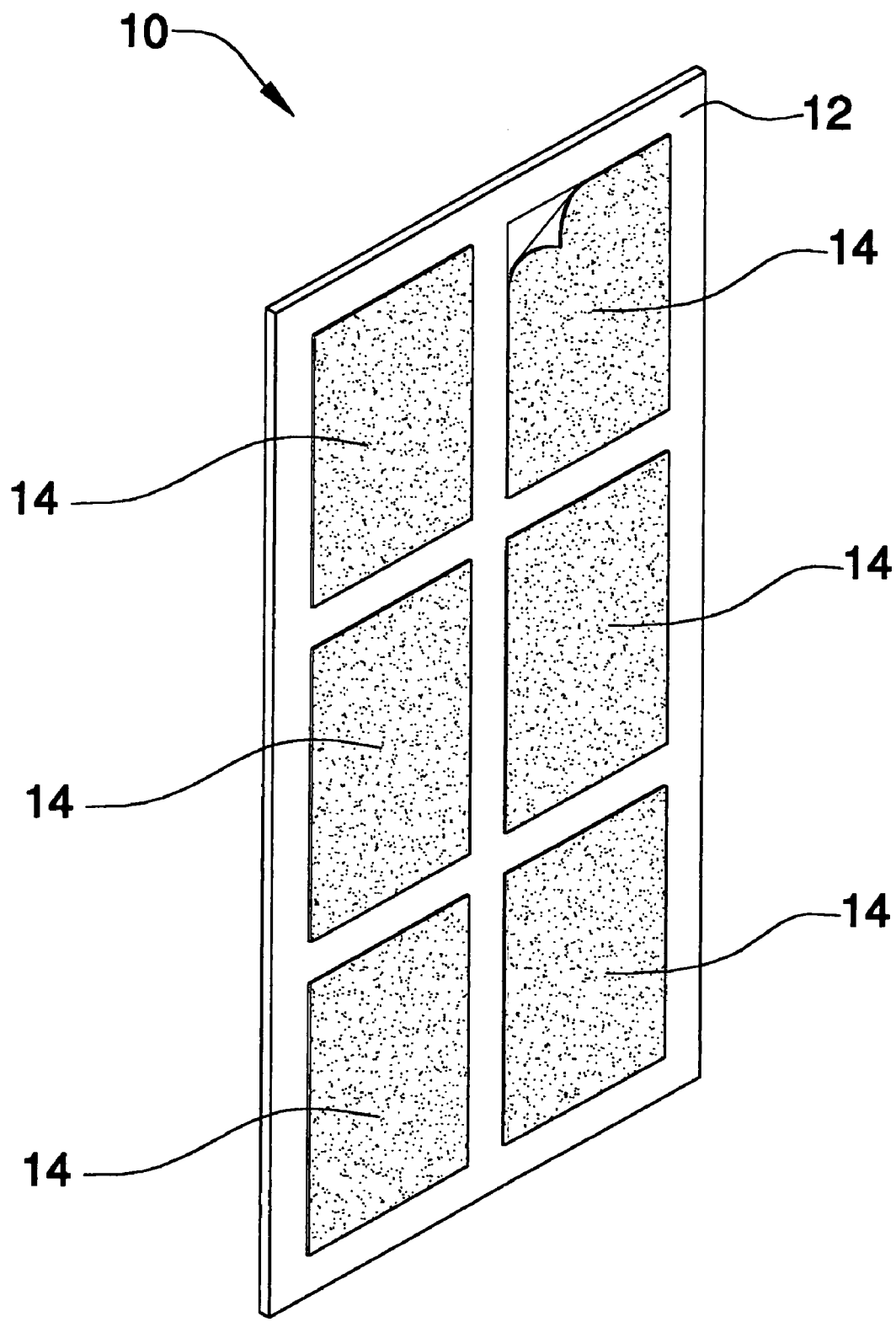
FIG. 7 is a perspective view of a preferred embodiment of the thin film medication device of the present invention.

Referring now to FIG. 7 which depicts a perspective view of a preferred embodiment of the thin film medication device 10 showing a support sheet 12; and a plurality of application strips 14 attached to the support sheet 12, wherein each strip can be pealed away from the support sheet 12.

Figure 8:
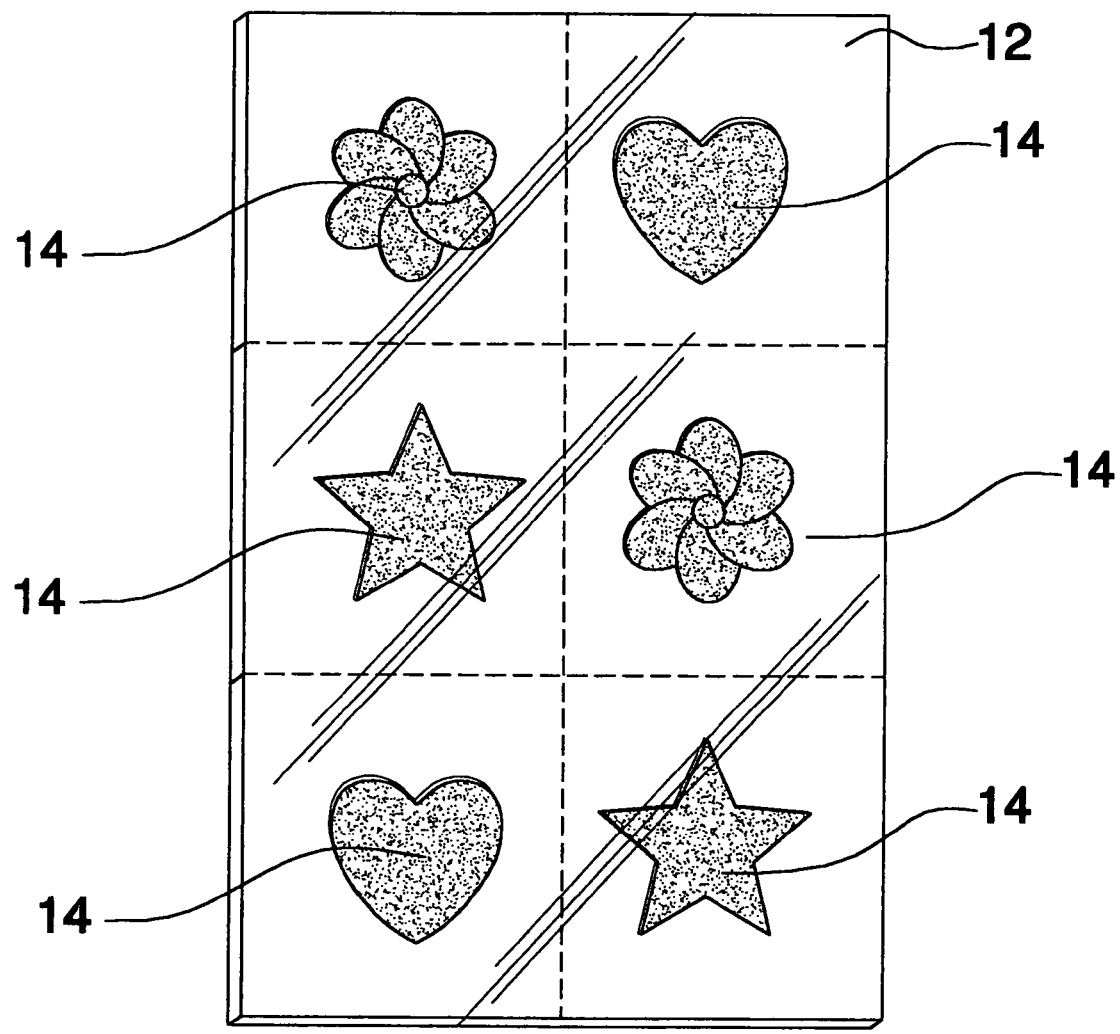
FIG. 8 is a front view of a preferred embodiment of the thin film medication device of the present invention.

Referring now to FIG. 8 which depicts a front view of a preferred embodiment of the thin film medication device 10 showing a support sheet 12; a plurality of application strips 14 attached to the support sheet 12, in which the geometric shape of each strip 14 may be configured in any number of different geometric shapes selected from the group consisting of a stylized heart, a stylized flower, and a stylized star.

As to the manner of usage and operation of the present invention, the same should be apparent from the above description. Accordingly, no further discussion relating to the manner of usage and operation will be provided.

While a preferred embodiment of the thin film medication device has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Throughout this specification, unless the context requires otherwise, the word "comprise" or variations such as "comprises" or "comprising" or the term "includes" or variations, thereof, or the term "having" or variations, thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of the steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A thin film medication device for therapeutic use, said device comprising:
   at least one support sheet; and
   a plurality of application strips attached to said support sheet, said strip comprising:
      a polymer base; and
      a therapeutic agent admixed with said polymer base.

2. The device of claim 1 further comprising a coloring agent admixed with said polymer base of said strip wherein said coloring agent is selected from the group consisting of FD&C Blue No. 1, FD&C Blue No. 2, FD&C Green No. 1, FD&C Green No. 2, FD&C Green No. 3, FD&C Orange No. 1, FD&C Red No. 1, FD&C Red No. 2, FD&C Red No. 3, FD&C Red No. 4, FD&C Red No. 32, FD&C Red No. 40, FD&C Yellow No. 1, FD&C Yellow No. 3, FD&C Yellow No. 4, FD&C Yellow No. 5, FD&C Yellow No. 6, and mixtures thereof.

3. The device of claim 1 further comprising a sweetening agent admixed with said polymer base of said strip, wherein said sweetening agent is selected from the group consisting of saccharin, aspartame, acesulfame K, sucrose, fructose, glucose, maltose, maltooligosaccharides, invert sugars, isomaltooligosaccharides, saccharified starch, isomerized sugars, dextrose, and mixtures thereof.

4. The device of claim 1 further comprising a conjugating agent admixed with said polymer base of said strip, wherein said conjugating agent is selected from the group consisting of ascorbic acid, sodium ascorbate, potassium ascorbate, calcium ascorbate, and mixtures thereof.

5. The device of claim 1 further comprising an osmotic disruptor admixed with said polymer base of said strip, wherein said osmotic disrupter is mannitol.

6. The device of claim 1 further comprising a cover attached to said support sheet and attached to said strip, wherein said cover is removable from said support sheet and from said strip.

7. The device of claim 6 wherein said cover is transparent cellophane which hermetically seals said strip.

8. The device of claim 1 further comprising a label affixed onto said support sheet.

9. The device of claim 1 further comprising a case containing said support sheet.

10. The device of claim 1 further comprising a plurality of support sheets.

11. The device of claim 1 wherein said polymer base of said strip is selected from the group consisting of a starch-based polymer, a lipid-based polymer, a glycerin-based polymer, protein-based polymer and mixtures thereof.

12. The device of claim 1 wherein said polymer base of said strip is selected from the group consisting of pullulan, hydroxypropylmethyl cellulose, hydroxyethyl cellulose, hydroxypropyl cellulose, polyvinyl pyrrolidone, carboxymethyl cellulose polyvinyl alcohol sodium alginate, polyethylene glycol, xanthane gum, tragacantha guar gum, acacia gum, arabic gum, polyacrylic acid, methylmethacrylate copolymer carboxyvinyl polymer and copolymers and mixtures thereof.

13. The device of claim 1 wherein said therapeutic agent is selected from the group consisting of an analgesic, a nonsteroidal anti-inflammatory agent, a steroid, a hormone, an antihistamine, a tranquilizer, an antidepressant, a hypnotic, a sedative, an antiepileptic, an awakening agent, a psychoneurotropic agent, a neuromuscular blocking agent, an antispasmodic agent, an antihistaminic, an antiallergic, a cardiotonic, an antiarrhythmic, a diuretic, a hypotensive, a vasopressor, an antitussive expectorant, a thyroid hormone, a sexual hormone, an antidiabetic, an antitumor agent, an antibiotic, a chemotherapeutic, a narcotic, a vaccine, a probiotic microorganism, and mixtures thereof.

14. The device of claim 1 wherein said therapeutic agent is a probiotic microorganism selected from the group consisting of *Lactobacillus acidophilus, Lactobacillus casei, Lactobacillus paracasei, Lactobacillus pediocci, Bifidobacterium bifidus, Bifidobacterium longum, Enterococcus faecium*, and *Saccharomyces boulardii* and other beneficial genera and species of probiotics.

15. The device of claim 1 wherein said polymer base of said strip comprises a hexatic phase micro thin material with an amorphous molecular orientation.

16. The device of claim 1, wherein each strip comprising said polymer base comprising about 40 to about 80 wt % of the strip; and said therapeutic agent comprising about 20 to about 40 wt % of the strip.

17. The device of claim 1 wherein said strip having a geometric shape selected from the group consisting of a stylized heart, a stylized flower, and a stylized star.

18. A kit for a thin film medication device for therapeutic use, said kit comprising:
   a plurality of support sheets; and
   a plurality of application strips attached to each support sheet, each strip comprising:
      a polymer base comprising about 40 to about 80 wt % of the strip; and
      a therapeutic agent admixed with the polymer base of the strip wherein the therapeutic agent comprising about 20 to about 40 wt % of the strip, wherein the therapeutic agent is a probiotic microorganism selected from the group consisting of *Lactobacillus acidophilus, Lactobacillus casei, Lactobacillus paracasei, Lactobacillus pediocci, Bifidobacterium bifidus, Bifidobacterium longum, Enterococcus faecium*, and *Saccharomyces boulard*; and
   a case containing the plurality of support sheets.

* * * * *